United States Patent
Woods

(10) Patent No.: US 6,217,612 B1
(45) Date of Patent: Apr. 17, 2001

(54) INTRAOCULAR LENS IMPLANT HAVING EYE ACCOMMODATING CAPABILITIES

(76) Inventor: Randall Woods, 230 Longbranch East, Prescott, AZ (US) 86303

( * ) Notice: Subject to any disclaimer, the term of this patent is extended or adjusted under 35 U.S.C. 154(b) by 0 days.

(21) Appl. No.: 09/393,514

(22) Filed: Sep. 10, 1999

(51) Int. Cl.[7] ....................................................... A61F 2/16
(52) U.S. Cl. ........................................ 623/6.37; 623/6.13
(58) Field of Search ................................. 623/6.11, 6.13, 623/6.14, 6.18, 6.37, 6.39

(56) References Cited

U.S. PATENT DOCUMENTS

| | | |
|---|---|---|
| 4,790,847 | 12/1988 | Woods . |
| 4,842,601 | 6/1989 | Smith . |
| 5,275,623 * | 1/1994 | Sarfarazi .............................. 623/6.39 |
| 5,674,282 | 10/1997 | Cumming . |

* cited by examiner

Primary Examiner—Dinh X. Nguyen
(74) Attorney, Agent, or Firm—Hovey, Williams, Timmons & Collins

(57) ABSTRACT

An intraocular lens (38) having focusing capabilities permitting focusing movement of the lens (38) in response to normal ciliary muscle movement incident to changes in the distance between the eye and an object under observation is provided. The lens (38) is designed for surgical implantation within the capsule (22) of an eye (10) and includes an optic (40) and a resilient body (46) which cooperate to form a discoid shaped lens (38) that generally conforms to the shape of the natural capsule (22). When distant objects are viewed, the ciliary body (32) is retracted and the capsule (22) flattens, thus causing the lens (38) to likewise flatten, moving the optic (40) posteriorly, closer to the fovea (26). When viewing near objects, the ciliary body (32) contracts, causing the capsule (22) and thus the lens (38) to expand to their original shape, shifting the optic (40) anteriorly, away from the fovea (26). The inventive lens (38) is preferably a unitarily formed, seamless body preferably comprising a flexible material which has elastic memory. Suitable materials comprise acrylates and silicone blends.

18 Claims, 1 Drawing Sheet

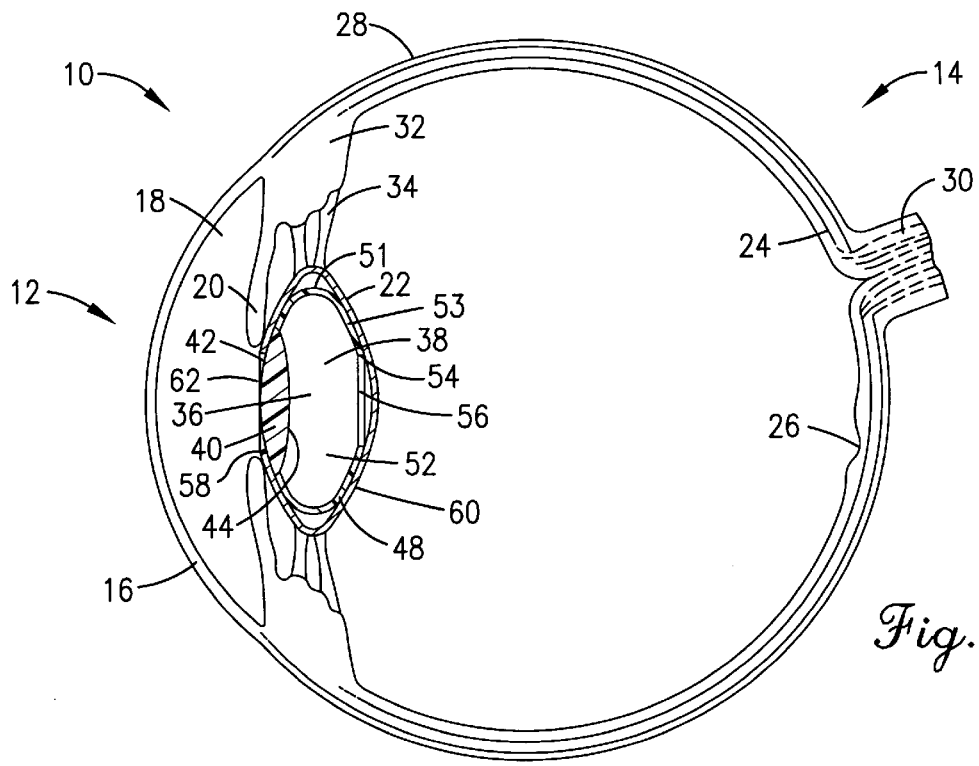
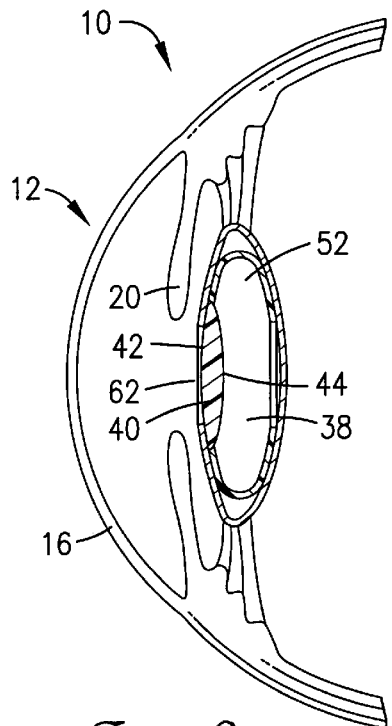
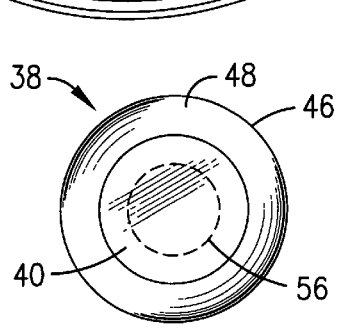
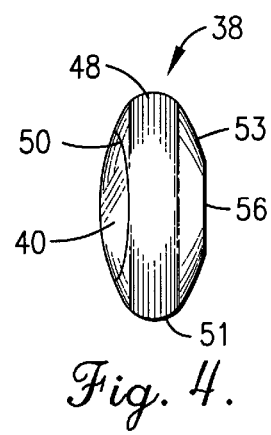
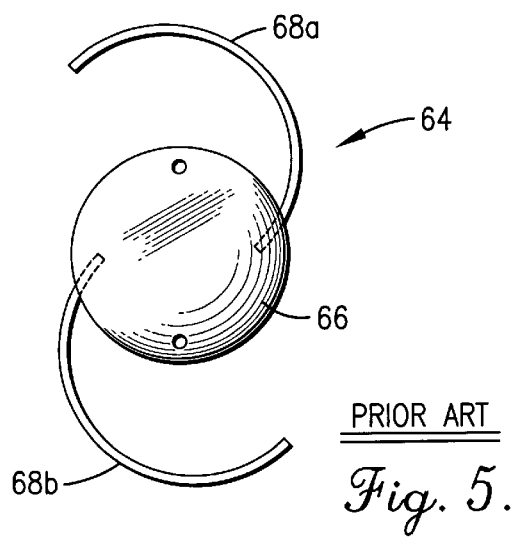

INTRAOCULAR LENS IMPLANT HAVING EYE ACCOMMODATING CAPABILITIES

BACKGROUND OF THE INVENTION

1. Field of the Invention

The present invention relates to accommodating intraocular lenses which can be surgically implanted as a replacement for the natural crystalline lens in the eyes of cataract patients.

2. Description of the Prior Art

Cataracts occur when the crystalline lens of the eye becomes opaque. The cataracts may be in both eyes and, being a progressive condition, may cause fading vision and eventual blindness. Cataracts were once surgically removed along with the anterior wall of the capsule of the eye. The patient then wore eyeglasses or contact lenses which restored vision but did not permit accommodation and gave only limited depth perception.

The first implant of a replacement lens within the eye occurred in 1949 and attempted to locate the replacement lens in the posterior chamber of the eye behind the iris. Problems such as dislocation after implantation forced abandonment of this approach, and for some period thereafter intraocular lenses were implanted in the anterior chamber of the eye.

Others returned to the practice of inserting the lens in the area of the eye posterior to the iris, known as the posterior chamber. This is the area where the patient's natural crystalline lens is located. When the intraocular lens is located in this natural location, substantially normal vision may be restored to the patient and the problems of forward displacement of vitreous humor and retina detachment encountered in anterior chamber intraocular lenses are less likely to occur. Lenses implanted in the posterior chamber are disclosed in U.S. Pat. Nos. 3,718,870, 3,866,249, 3,913,148, 3,925,825, 4,014,049, 4,041,552, 4,053,953, and 4,285,072. None of these lenses have focusing capability.

Lenses capable of focusing offered the wearer the closest possible substitute to the crystalline lens. U.S. Pat. No. 4,254,509 to Tennant discloses a lens which moves in an anterior direction upon contraction of the ciliary body and which is located anterior to the iris. Though providing focusing capabilities, it presents the same disadvantages as other anterior chamber lenses. U.S. Pat. No. 4,253,199 to Banko approaches the problem of providing a focusable lens differently, by providing a replacement lens of deformable material sutured to the ciliary body. This lens functions much as the original crystalline lens but risks bleeding from the sutures.

U.S. Pat. No. 4,409,691 to Levy is asserted to provide a focusable intraocular lens positioned within the capsule. This lens is located in the posterior area of the capsule and is biased toward the fovea or rear of the eye. The '691 lens is deficient because it requires the ciliary muscle to exert force through the zonules on the capsule in order to compress the haptics inward and drive the optic forward for near vision. However, the ciliary muscles do not exert any force during contraction because the zonules, being flexible filaments, exert only tension, not compression on the capsule. The natural elasticity of the lens causes the capsule to become more spherical upon contraction of the ciliary muscle. Thus, there is no inward force exerted on the capsule to compress the haptics of the Levy lens, and therefore accommodate for near vision. Even if such force were somehow available, the Levy lens' haptics are loaded inward when accommodating for near vision. Since accommodation for near vision is the normal status of the capsule, the Levy lens' haptics are loaded, reducing the fatigue life of the springlike haptics.

U.S. Pat. No. 5,674,282 to Cumming is directed towards an accommodating intraocular lens for implanting within the capsule of an eye. The Cumming lens comprises a central optic and two plate haptics which extend radially outward from diametrically opposite sides of the optic and are movable anteriorly and posteriorly relative to the optic. However, the Cumming lens suffers from the same shortcomings as the Levy lens in that the haptics are biased anteriorly by pressure from the ciliary bodies. This will eventually lead to pressure necrosis of the ciliary body.

Finally, U.S. Pat. No. 4,842,601 to Smith discloses an accommodating intraocular lens having anterior and posterior members which urge against the anterior and posterior walls of the natural lens capsule. The muscular action exerted on the natural capsule will thus cause the lens to flatten, thereby changing the focus thereof. The Smith lens is formed of first and second plastic lens members connected to one another adjacent their peripheral edges so as to provide a cavity therebetween. The connection between the lens members is accomplished by way of a U-shaped flange on the first member which forms an inwardly facing groove for receiving an outwardly extended flange on the second member. The Smith lens is lacking in that the first and second members must be separately inserted into the capsule and assembled within the capsule which is extremely difficult for even highly skilled surgeons to accomplish.

There is a need for an intraocular lens implant capable of focusing in a manner similar to the natural lens. This lens implant should be readily insertable into the capsule and should last for a substantial number of years without damaging any of the eye components.

OBJECTS AND SUMMARY OF THE INVENTION

The present invention fills this need by providing an intraocular lens with focusing capabilities which is safe for long-term use in an eye.

In more detail, the lens of the invention comprises an optic presenting a convex anterior surface and a resilient optic positioning element or body coupled to the optic to cooperatively present a discoid shaped lens that generally conforms to the shape of the natural eye capsule. The optic positioning element presents a posterior face that engages the posterior wall of the natural capsule, and an anterior face that engages the anterior wall of the natural capsule. The anterior and posterior faces of the optic positioning element are joined together by a bight.

As a result of the size and shape of the inventive lens, the focusing action of the natural lens is simulated. That is, the ciliary body of the eye (which remain connected to the capsule) continues to exert a muscular force radially outward from the center of the capsule through the zonular fibers so as to flatten the capsule. Because the posterior and anterior walls of the capsule are engaging the anterior and posterior faces of the optic positioning element, the inventive lens flattens in a manner similar to the natural capsule. This flattening alters the distance between the optic of the inventive lens and the fovea of the eye, thus allowing distant objects to be viewed.

The optic and optic positioning element can be formed of any biologically inert material conventionally used in intraocular lens construction, (e.g., yieldable synthetic resin materials). Examples of suitable lens materials include acrylates (such as polymethylmethacrylates), silicons, and mixtures of acrylates and silicons. It is particularly preferred that lenses according to the invention be constructed of a material having an elastic memory (i.e., the material should be capable of substantially recovering its original size and shape after a deforming force has been removed). An example of a preferred material having elastic memory is MEMORYLENS (available from Mentor Ophthalmics in California).

BRIEF DESCRIPTION OF THE DRAWING FIGURES

FIG. 1 is a vertical sectional view showing placement of the lens of the invention within the capsule of an eye, with the eye focused on an object near the viewer;

FIG. 2 is a vertical sectional view showing the location of the lens of FIG. 1 within the capsule of the eye, focused on an object distant from the viewer;

FIG. 3 is a front view of an inventive lens shown in its original resting, non-flattened state;

FIG. 4 is a side elevational view of the lens of FIG. 3; and

FIG. 5 is a front view of a prior art accommodating lens having a pair of haptics on the optic.

DETAILED DESCRIPTION OF THE PREFERRED EMBODIMENTS

Referring now to the drawings, the present invention is in the form of an intraocular lens for surgical replacement of the human lens in the treatment of cataracts in the human eye. FIG. 1 shows the various components of the human eye pertinent to this invention. Briefly, the eye 10 includes a frontal portion 12 and a rearward portion 14. The frontal portion 12 of the eye 10 is covered by a cornea 16 which encloses and forms an anterior chamber 18. The anterior chamber 18 contains aqueous fluid and is bounded at the rear by an iris 20. The iris 20 opens and closes to admit appropriate quantities of light into the inner portions of the eye 10. The eye 10 includes a capsule 22 which ordinarily contains the natural crystalline lens. When the eye 10 focuses, the capsule 22 changes shape to appropriately distribute the light admitted through the cornea 16 and the iris 20 to a retina 24 at the rearward portion 14 of the eye 10.

The retina 24 is composed of rods and cones which act as light receptors. The retina 24 includes a fovea 26 which is a rodless portion that provides for acute vision. The outside of the rearward or posterior portion 14 of the eye 10 is known as the sclera 28 which joins into and forms a portion of the covering for the optic nerve (designated by numeral 30). Images received by the retina 24 are transmitted through the optic nerve 30 to the brain. The area between the retina 24 and the capsule 22 is occupied by vitreous fluid. Finally, the eye 10 includes a ciliary muscle or body 32 having zonular fibers 34 (also referred to as zonules) which are attached to the capsule 22.

Ocular adjustments for sharp focusing of objects viewed at different distances is accomplished by the action of the ciliary body 32 on the capsule 22 and crystalline lens (which would be located at numeral 36 in the natural, unmodified eye) through the zonular fibers 34. The ciliary body 32 contracts, allowing the capsule 22 to return to a more spherical shape for viewing objects that are nearer the viewer. When the ciliary body 32 retracts and pulls on the zonular fibers 34 to make the capsule 22 more discoid, objects at a distance can be viewed in proper focus.

Referring to FIGS. 1–4, the inventive lens is an accommodating lens 38 which includes a central optic 40. The optic 40 comprises an anterior surface 42 and a posterior surface 44. The anterior surface 42 and the posterior surface 44 are usually convex, although the shape of these surfaces and size of the optic 40 can be varied depending upon the user's eyesight. The lens 38 further includes a resilient body 46. Resilient body 46 comprises an outer wall 48 which extends radially from optic 40. Resilient body 46 is preferably integral and essentially flush with optic 40 at optic perimeter 50 where wall 48 joins optic 40. Wall 48 then curves to form a bight 51, and converges on the posterior side 53 of lens 38. Wall 48 forms a chamber 52 and terminates at location 54 to form an opening 56 which communicates with the chamber 52 allowing fluids to enter and fill the chamber 52.

The overall shape of lens 38 in its original resting, non-deformed shape generally conforms to the shape of capsule 22 when capsule 22 is focused to view an object near the viewer (FIG. 1). Outer wall 48 of the resilient body 46 cooperates with optic 40 to form a lens having an overall discoid or saucer-like shape as best shown in FIGS. 3–4. The lens 38 is of sufficient size so that optic 40 mildly urges against the anterior wall 58 of the capsule 22, while the posterior side 53 of lens 38 urges against the posterior wall 60 of the capsule 22.

Intraocular lens 38 substitutes both locationally and functionally for the original, natural, crystalline lens (which would normally be at location 36). To insert the lens 38 into the capsule 22, an ophthalmic surgeon would remove the natural lens (and thus the cataracts) by conventional methods, leaving an opening 62 in the anterior wall 58 of the capsule 22. Lens 38 is then folded into a compact size for insertion into the capsule 22 through the opening 62. Once inserted, the capsule 22 is filled with fluids (e.g., saline solution) which enter the chamber 52 of the lens 38, causing the lens 38 to return to its original, non-deformed state as shown in FIG. 1. There is no need to suture the lens to the capsule 22 because, due to the size and shape of the lens 38 as described above, the lens 38 will not rotate or shift within the capsule 22.

Implantation of the inventive lens 38 restores normal vision because, not only does the lens 38 replace the patients occluded natural lens, but the normal responses of the ciliary body 32 cooperate with the lens 38 during focusing. In FIG. 1, the focal length between the posterior surface 44 of optic 40 and the fovea 26 is greater to permit viewing of nearby objects. The focal length is greater because the ciliary muscle or body 32 has contracted, making the capsule 22 more spheroid, permitting the lens 38 to be maintained in its resting state and positioning the optic 40 towards the anterior wall 58. The lens 38 of the present construction thus follows the eye's natural physiology for focusing to provide a substitute means of optical accommodation. When the object of observation becomes more distant, the sensory cells within the retina 24 signal the ciliary body 32 to relax, thus pulling on the zonular fibers 34 to make the capsule more discoid as shown in FIG. 2. In so doing, the horizontal depth of the capsule 22 is narrowed, which in turn causes the horizontal depth of the lens 38 to narrow in a similar manner. This narrowing causes the optic 40 to move posteriorly as the capsule 22 and the lens 38 become more discoid. The focal length between the posterior surface 44 of optic 40 and the fovea 26 is thus shortened, and the object remains in focus. If the object under observation reapproaches the eye, the ciliary body 32 again contracts, lessening the tension on the zonular fibers 34. When this occurs, the lens 38 returns to its resting, non-deformed shape (as shown in FIGS. 1 and 4), thus moving the optic 40 anteriorly. The focal length between the posterior surface 44 of the optic 40 and the fovea 26 is thus increased (see FIG. 1), and the object remains in focus.

In view of the foregoing discussion, it will be appreciated that the inventive lens 38 is designed so as to provide a substantially uniform distribution of pressure along the walls of the capsule 22. This was often not the case in prior art intraocular lenses. For example, FIG. 5 depicts one prior art lens 64 comprising an optic 66 and haptics 68a,b. The lens 64 is designed for placement within the natural capsule, with the haptics 68a,b providing a means for biasing the optic 66 anteriorly during focusing. However, due to the design of the lens 64, the haptics 68a,b apply pressure along concentrated portions of the capsule, thus causing wear on the capsule. This problem is avoided with the lens of the invention.

Although the invention has been described with reference to the preferred embodiment illustrated in the attached drawing figures, it is noted that equivalents may be employed and substitutions made herein without departing from the scope of the invention as recited in the claims. For example, while the foregoing method of inserting the lens 38 into the capsule 22 presumed that a portion of the anterior wall 58 of the capsule 22 would be removed with the natural lens, it will be appreciated that it may be possible to insert the lens 38 through an incision in the anterior wall 58. Furthermore, while the foregoing description discloses that the lens 38 could be utilized in cataract patients, the lens 38 may be used in any situation where the natural lens needs to be replaced (e.g., in a patient who wishes to eliminate the need for bifocals).

Having thus described the preferred embodiment of the invention, what is claimed as new and desired to be protected by Letters Patent includes the following:

1. An accommodating intraocular lens for implantation substantially within the confines of the capsule of a human eye between the anterior and posterior capsule walls, said lens comprising:
   an optic presenting an anterior surface; and
   a resilient optic positioning element coupled to the optic to cooperatively present a discoid shape that generally conforms to the shape of the capsule,
      said optic positioning element presenting a posterior face that is configured for yieldable engagement with the posterior capsule wall, an anterior face that is generally flush with the anterior surface of the optic and configured for yieldable engagement with the anterior wall of the capsule, and a bight joining the anterior and posterior faces,
      said optic positioning element being unitarily formed,
      said optic positioning element posterior face, said optic positioning element anterior face, and said bight cooperatively forming a chamber within said optic positioning element,
      said optic positioning element posterior face including an opening therethrough, said opening communicating with said chamber so as to allow fluids to enter and fill the chamber.

2. The lens of claim 1, said optic positioning element comprising a seamless body.

3. The lens of claim 1, said optic presenting a convex anterior surface.

4. The lens of claim 1, said optic positioning element being formed of a yieldable synthetic resin material.

5. The lens of claim 1, said optic positioning element being formed of a material comprising a compound selected from the group consisting of silicon, polymethylmethacrylates, and mixtures thereof.

6. The lens of claim 1, wherein said optic positioning element is formed of a material having an elastic memory.

7. The lens of claim 1, said anterior capsule wall having an opening therethrough, said opening and said optic having respective diameters, said optic diameter being greater than said capsule wall opening diameter.

8. The lens of claim 1, wherein said optic positioning element comprises an equator located approximately midway between said optic and said optic positioning element posterior face, said equator being continuous and without openings formed therein.

9. A single-optic, accommodating intraocular lens for implantation substantially within the confines of the capsule of a human eye between the anterior and posterior capsule walls, said lens comprising:
   only one optic, said one optic presenting an anterior surface; and
   a resilient optic positioning element coupled to the optic to cooperatively present a discoid shape that generally conforms to the shape of the capsule,
      said optic positioning element presenting a posterior face that is configured for yieldable engagement with the posterior capsule wall, an anterior face that is generally flush with the anterior surface of the optic and configured for yieldable engagement with the anterior wall of the capsule, and a bight joining the anterior and posterior faces,
      said optic positioning element being unitarily formed.

10. The lens of claim 9, said optic positioning element comprising a seamless body.

11. The lens of claim 9, said optic presenting a convex anterior surface.

12. The lens of claim 9, said optic positioning element being formed of a yieldable synthetic resin material.

13. The lens of claim 9, said optic positioning element being formed of a material comprising a compound selected from the group consisting of silicon, polymethylmethacrylates, and mixtures thereof.

14. The lens of claim 9, wherein said optic positioning element is formed of a material having an elastic memory.

15. The lens of claim 9, said anterior capsule wall having an opening therethrough, said opening and said optic having respective diameters, said optic diameter being greater than said capsule wall opening diameter.

16. The lens of claim 9, wherein said optic positioning element posterior face, said optic positioning element anterior face, and said bight cooperatively form a chamber within said optic positioning element.

17. The lens of claim 16, wherein said optic positioning element posterior face includes an opening therethrough, said opening communicating with said chamber.

18. The lens of claim 9, wherein said optic positioning element comprises an equator located approximately midway between said optic and said optic positioning element posterior face, said equator being continuous and without openings formed therein.

* * * * *